US009278169B2

(12) United States Patent
Strueber

(10) Patent No.: US 9,278,169 B2
(45) Date of Patent: *Mar. 8, 2016

(54) AMBULATORY LUNG ASSIST DEVICE WITH IMPLANTED BLOOD PUMP AND OXYGENATOR

(71) Applicant: HeartWare, Inc., Miami Lakes, FL (US)

(72) Inventor: Martin Strueber, Schwueblingsen (DE)

(73) Assignee: HeartWare, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/657,461

(22) Filed: Mar. 13, 2015

(65) Prior Publication Data
US 2015/0182681 A1 Jul. 2, 2015

Related U.S. Application Data

(63) Continuation of application No. 13/857,254, filed on Apr. 5, 2013, now Pat. No. 9,011,311.

(60) Provisional application No. 61/621,291, filed on Apr. 6, 2012.

(51) Int. Cl.
*A61M 1/32* (2006.01)
*A61M 1/36* (2006.01)
(Continued)

(52) U.S. Cl.
CPC ............... *A61M 1/32* (2013.01); *A61M 1/101* (2013.01); *A61M 1/122* (2014.02); *A61M 1/14* (2013.01); *A61M 1/3666* (2013.01); *A61M 1/1698* (2013.01)

(58) Field of Classification Search
None
See application file for complete search history.

(56) References Cited

U.S. PATENT DOCUMENTS 4,927,407 A  5/1990  Dorman
7,699,586 B2  4/2010  LaRose et al.
(Continued)

FOREIGN PATENT DOCUMENTS

WO  8702894 A2  5/1987
WO  2006031858 A1  3/2006

OTHER PUBLICATIONS

International Search Report issued by the International Searching Authority (ISA/US) on Jun. 26, 2013 in connection with International Application No. PCT/US2013/035484.
(Continued)

Primary Examiner — Brian T Gedeon
Assistant Examiner — Ankit Tejani
(74) Attorney, Agent, or Firm — Lerner, David, Littenberg, Krumholz & Mentlik, LLP

(57) ABSTRACT

The present disclosure provides a system for oxygenating blood. The system may include an implantable blood pump that may draw a supply of blood from the circulatory system of a mammalian subject, such as a human being. The blood pump may provide the supply of blood to an adaptor, where the supply of blood may be supplied to either or both of a first branch or second branch. The first branch may lead to an external blood oxygenator. The oxygenator may oxygenate the blood, and the blood may be returned to the circulatory system of the mammalian subject. The second branch may bypass the oxygenator and may connect to the circulatory system of the mammalian subject. In this regard, while the blood is supplied to the second branch, the oxygenator may be disconnected and blood may be prevented from entering the first branch.

32 Claims, 3 Drawing Sheets

(51) Int. Cl.
*A61M 1/10* (2006.01)
*A61M 1/14* (2006.01)
*A61M 1/12* (2006.01)
*A61M 1/16* (2006.01)

(56) References Cited

U.S. PATENT DOCUMENTS

| | | |
|---|---|---|
| 7,896,832 B2 | 3/2011 | Zafirelis et al. |
| 7,972,122 B2 | 7/2011 | LaRose et al. |
| 8,007,254 B2 | 8/2011 | LaRose et al. |
| 2002/0057989 A1 | 5/2002 | Afzal et al. |
| 2004/0052681 A1 | 3/2004 | Mortensen et al. |
| 2006/0245959 A1 | 11/2006 | LaRose et al. |
| 2006/0284423 A1 | 12/2006 | Katsuno et al. |
| 2007/0161845 A1 | 7/2007 | Magovern et al. |
| 2010/0185136 A1 | 7/2010 | Thomas |

OTHER PUBLICATIONS

Written Opinion of the International Searching Authority issued by the International Searching Authority (ISA/US) on Jun. 26, 2013 in connection with International Application No. PCT/US2013/035484.

Zhang et al., "A novel wearable pump-lung device: in vitro and acute in vivo study," J. of Heart & Lung Transplantation (Aug. 22, 2011) pp. 101-105.

Extended European Search Report for Application No. EP13772625 dated Oct. 27, 2015.

AMBULATORY LUNG ASSIST DEVICE WITH IMPLANTED BLOOD PUMP AND OXYGENATOR

CROSS-REFERENCE TO RELATED APPLICATIONS

The present application is a continuation of U.S. patent application Ser. No. 13/857,254, filed Apr. 5, 2013 which claims the benefit of U.S. Provisional Patent Application No. 61/621,291, filed Apr. 6, 2012, the disclosure of which is hereby incorporated herein by reference.

BACKGROUND OF THE INVENTION

Certain lung diseases, such as emphysema, reduce the ability of a person's lungs to sufficiently oxygenate blood. If parts of a patient's lungs are removed due to conditions such as lung cancer, the ability to oxygenate blood is impaired. Persons having such conditions require assistance in providing oxygenated blood to their bodies. Some patients with such conditions can survive if oxygen-enriched air is supplied to their lungs, as by use of an oxygen mask. However, other patients do not have sufficient lung capacity for survival with these measures.

It has been proposed to provide blood oxygenators to such patients. A blood oxygenator is a device which exposes the patient's blood to air or oxygen as the blood flows through the device. Blood oxygenators have long been used as a component of the so-called "heart-lung machine" to provide short-term support to a patient during surgical procedures such as heart surgery or transplantation. However, the systems incorporating such oxygenators require frequent and professional maintenance, and are suitable for use only in a hospital setting. These systems typically require that the patient be confined to a bed, which drastically impairs the patient's quality of life. Thus, there has been a significant need in the art for a patient support system using an oxygenator which can be used for long-term treatment, desirably outside of a hospital environment.

BRIEF SUMMARY OF THE INVENTION

One aspect of the disclosure provides a system for oxygenating blood. The system may include a blood pump having an outlet and an inlet adapted for communication with the circulatory system of a mammalian subject at an inlet location. The system may further include one or more return fittings adapted for communication with the circulatory system of the subject at one or more return locations remote from the inlet location. The system may further include a blood oxygenator having a blood inlet releasably connectable in communication with the outlet of the pump and a blood outlet releasably connectable in communication with one of said return fittings. The system may further include a bypass conduit adapted to connect the outlet of the pump in communication with one of said return fittings at least when the oxygenator is disconnected.

In one variation, the system further includes an oxygenator inlet disconnect fitting connected to the outlet of the blood pump and an oxygenator outlet disconnect fitting connected to one of said return fittings, the blood inlet and outlet of the oxygenator being adapted to releasably engage the disconnect fittings.

In another variation, the system further includes an adaptor having an inlet connected to the outlet of the blood pump, a first branch connected to the oxygenator inlet disconnect fitting and a second branch connected the bypass conduit.

In another variation, the system further includes a valve in the adaptor having a normal condition in which blood flow entering the adaptor is directed primarily to the first branch and a bypass condition in which blood flow is directed primarily to the second branch.

In another variation, the system further includes a valve connected in series with the bypass conduit, the valve having a normal condition in which flow through the bypass conduit is at least partially blocked and a bypass condition in which flow through the bypass conduit is substantially unblocked.

In another variation, when the valve is in the normal condition, flow through the bypass conduit is only partially blocked.

In another variation, the pump is an implantable pump configured to be implanted within a mammalian subject body.

In another variation, the implantable pump is biocompatible.

In another variation, the pump is selected from a group consisting of: an axial-flow blood pump, and centrifugal blood pump.

In another variation, at least one of the one or more return locations is selected from a group consisting of: a right atrium, a right ventricle, or a pulmonary artery.

In another variation, the inlet location is a pulmonary artery.

In another variation, the bypass conduit is configured to be at least partially disposed within the mammalian subject body.

In another variation, an internal diameter of the first branch is different than an internal diameter of the second branch.

In another variation, the internal diameter of the first branch is larger than the internal diameter of the second branch.

Another aspect of the disclosure provides a method of providing respiratory assistance to a mammalian subject. The method includes (a) directing blood from an inlet location in the circulatory system of the subject through a pump, through an oxygenator and back to the circulatory system. The method may further include (b) temporarily disconnecting the oxygenator. The method may further include (c) directing blood through the pump and through a bypass conduit back to the circulatory system. The method may further include (d) reconnecting the same oxygenator or a different oxygenator and then resuming step (a).

In one variation, steps (b), (c) and (d) are performed so that blood continuously flows through the pump.

In another variation, in step (c), the blood is directed back to the pulmonary artery of the subject.

In another variation, in step (a), the blood is directed back to the pulmonary artery of the subject.

In another variation, the method further includes the step of directing blood through the bypass conduit and back to the circulatory system during step (a).

In another variation, during step (a), blood passes through the oxygenator at a first rate and blood passes through the bypass conduit at a second rate less than the first rate.

DETAILED DESCRIPTION

Figure 1:
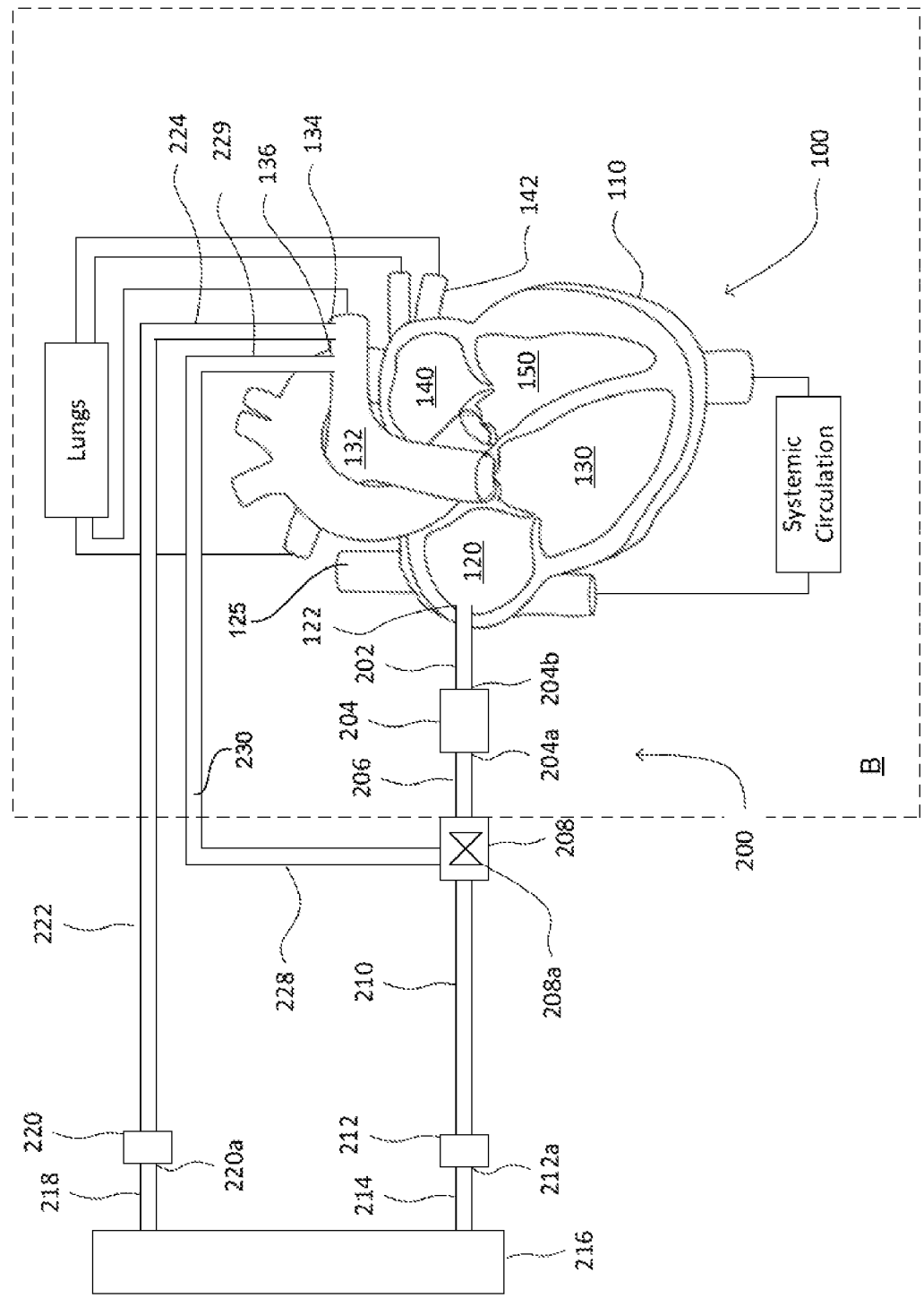
FIG. 1 is a diagrammatic view of a system according to one embodiment of the invention in conjunction with the circulatory system of a patient.

A system 200 according to one embodiment of the invention includes a blood pump 204 having a pump inlet 204b and a pump outlet 204a. The blood pump 204 desirably is a pump suitable for providing pumping action over a long period of time, such as months or years, without severe hemolysis or other severe effects on the blood. Pumps of the type used to provide long-term assistance to the heart, sometimes referred to as "ventricular assist devices" or "VADs" can be used. The pump desirably is a load-sensitive pump having a flow versus pressure characteristic such that the flow through the pump decreases progressively with the pressure head opposing the flow. Stated another way, the pump desirably is not a positive-displacement pump. Impeller pumps such as centrifugal or axial-flow impeller pumps can be used. The pump desirably is arranged so that it can be carried by the patient and powered by a portable power supply. Most desirably, the pump is implantable within the body of the patient. Implantable blood pumps are described in U.S. Pat. Nos. 7,699,586, 7,972,122, and 8,007,254, the disclosures of which are incorporated by reference herein. For example, an axial-flow impeller pump of the type supplied by HeartWare, Inc. of Miami Lakes, Fla. under the trademark MVAD can be used.

A pump inlet conduit 202 is connected to pump inlet 204b. The pump and the inlet conduit are arranged so that the pump inlet 204b can be connected to an inlet location 122 within the circulatory system of the subject.

The system further includes a pump outlet conduit 206 having one end connected to the outlet 204a of the pump and having the other end connected to a branching adaptor 208. Adaptor 208 has a single inlet connected to pump outlet conduit 206 and has two outlets. A first outlet of adaptor 208 is connected to an oxygenator supply conduit 210, also referred to as a first branch. The second outlet of adaptor 208 is connected to a bypass conduit 228, also referred to as a second branch. Adaptor 208 includes a valve 208a that can be actuated between a first position in which the flow of blood entering the adaptor is directed primarily to first branch 210, and a second position in which the flow is directed primarily or entirely to or second branch 226.

Oxygenator supply conduit 210 extends to an oxygenator inlet disconnect fitting 212. Disconnect fitting 212 includes an interface arranged to releasably connect conduit 210 in communication with a mating fitting 212a and form a fluid-tight seal with the mating fitting when connected. The disconnect fitting may also include an internal valve (not shown) arranged to block flow through the disconnect and conduit 210 when the mating fitting is disconnected. The system further includes an oxygenator outlet disconnect fitting 220 similar to fitting 212. Outlet disconnect fitting 220 is connected to one end of an oxygenator return conduit 222. Fitting 220 is adapted to releasably engage a mating fitting 220a in a fluid-tight seal so as establish communication between fitting 220a and conduit 222. Disconnect fitting 220 may also include a valve (not shown) for closing the end of conduit 222 when fitting 220a is disconnected. Merely by way of example, suitable disconnect fittings are commercially available from NovaLung GmbH of Baden-Württemburg, Germany.

An oxygenator 216 has a blood inlet 214 with a fitting 212a mateable with oxygenator inlet disconnect fitting 212, and has a blood outlet 218 with a fitting 220a mateable with outlet disconnect fitting 220. Oxygenator 216 is configured to remove carbon dioxide from blood passing through the oxygenator, and to supply oxygen to the blood. For example, the internal construction of oxygenator 216 may be the same as that of a QUADROX® Oxygenator System manufactured by Maquet. The oxygenator 216 may include subcomponents typically associated with an oxygenator, such as a permeable membrane and oxygen supply. The oxygenator desirably is arranged so as to be portable and allow the patient to move about while connected to the oxygenator. For example, the oxygenator may be coupled to a portable oxygen supply such as a cylinder (not shown). Desirably, the oxygenator and supply may be carried on a mobile cart or on a harness worn by the patient.

Oxygenator return conduit 222 has a return fitting 224 at the end of the conduit remote from disconnect 220. The return fitting is adapted for connection to the circulatory system. For example, return fitting 224 may be an end of the conduit adapted for insertion into the vasculature of the patient. Bypass conduit 228 has a similar return fitting 229 at the end of the bypass conduit remote from adaptor 208.

In the condition depicted in FIG. 1, the system is in place in a mammalian subject such as a human patient in need of respiratory assistance. Pump 204 is implanted within the body of the patient, with inlet conduit 202 connected to the circulatory system 100 of the subject at an inlet location 122 such as the right atrium 120 of the heart or the right ventricle 130, so that the inlet 204b of pump 204 is in communication with the circulatory system at the inlet location. Return fittings 224 and 229 and the adjacent portions of conduits 222 and 230 are also implanted in the body of the subject. The return fittings communicate with the circulatory system of the subject at return locations 134 and 136, respectively. The return locations may be remote from the inlet location. For example, the return locations may be in the pulmonary artery 132 of the subject. Adaptor 206 and disconnect fittings 212 and oxygenator 216 are disposed outside of the subject's body. In a normal condition, oxygenator 216 is connected to disconnect fittings 212 and 220.

With the system in place, the subject's heart 110 continues to pump blood in the normal manner. The right atrium 120 collects oxygen-depleted blood from the systemic circulatory system of the body B. The oxygen-depleted blood flows from the right atrium 120 to the right ventricle 130. The blood is then pumped into the lungs via the pulmonary artery 132 where the blood is oxygenated and where carbon dioxide is removed from the blood. The oxygenated blood is then returned to the left atrium 140 via the pulmonary veins 142. The blood is pumped from the left atrium to the left ventricle 150, and then pumped by the left ventricle and to systemic circulation. After passing through the systemic circulation, the blood becomes oxygen-depleted and returns to the right atrium 120 via the vena cava 125, where the process begins again.

Pump 204 draws some of the blood from the circulatory system 100 of the subject at the inlet location 122. For example, the flow rate of blood through the pump 204 may be approximately 2 to 5 L/min. In the normal condition, with the oxygenator in place, the blood passing out of pump 204 passes primarily through the first branch, through oxygenator supply conduit 210, oxygenator 216 and oxygenator return conduit 222 to return fitting 224, and re-enters the circulation at return location 134 in the pulmonary artery. Oxygenator 216 supplies oxygen to the blood passing along first branch 210 and removes some of the carbon dioxide present in the blood. The oxygenation and carbon dioxide removal provided by the oxygenator supplement the action of the subject's lungs.

Valve 208a of adaptor 208 desirably is arranged to allow a relatively small portion of the blood supplied by pump 204 to pass through the second branch, through bypass conduit 228 and back to the circulatory system at return fitting 229 and return location 136, while the system is in the normal condition and the valve is in the first position. This flowing blood helps to keep the second branch free of thrombus.

The oxygenator must be replaced periodically. To change the oxygenator, the system is brought to a bypass condition by adjusting valve 208a of the adaptor to the second position. In this condition, the blood passing from pump 204 is directed entirely along the second branch, through the bypass conduit 228 and back to the circulatory system via return fitting 229 at return location 134. While the system is in this bypass condition, fittings 212a and 220a of the oxygenator are disconnected from disconnect fittings 212 and 220, and a new oxygenator is connected to the disconnect fittings. Once the new oxygenator is in place, the system is returned to the normal condition by readjusting valve 208a to the first position. Manipulating the valve and actuating the disconnect fittings are routine tasks which do not require a high level of skill. Desirably, these elements are arranged so that the oxygenator can be changed by the patient or by a medical technician or nurse without extensive training.

While the system is in the bypass condition, pump 204 continues to operate and blood continues to flow through the pump and through the bypass conduit. The pump thus assists blood circulation through the lungs. This assistance enhances the gas exchange function of the lungs, which helps the subject to survive during the time the system is in the bypass condition. The continued flow of blood through the pump in the bypass condition helps keep the pump free of thrombus. The continued flow of blood through the pump also helps to protect the pump from damage. Certain impeller-type blood pumps use hydrodynamic bearings, magnetic bearings or both to maintain the impeller suspended and out of contact with surrounding parts. While the pump is running, the impeller and surrounding parts do not suffer from mechanical wear, but starting and stopping the pump renders the bearings ineffective and causes wear. The continued flow of blood through the pump in the bypass condition allows the pump to continue running without prolonged exposure of blood in the pump to the relatively severe hydrodynamic conditions in the pump.

In a system according to a further embodiment of the invention, the valve in adaptor 208 may be arranged to direct the entire flow of blood through the first branch and thus through the oxygenator 216 in the normal condition. In a further variant, adaptor 208 and valve 208a may be implanted within the body provided that the valve can be controlled from outside of the body. For example, the valve may be disposed near the skin so that it can be manipulated through the skin. Alternatively, the valve may be provided with an electrically operated or fluid-operated actuation mechanism.

Figure 2:
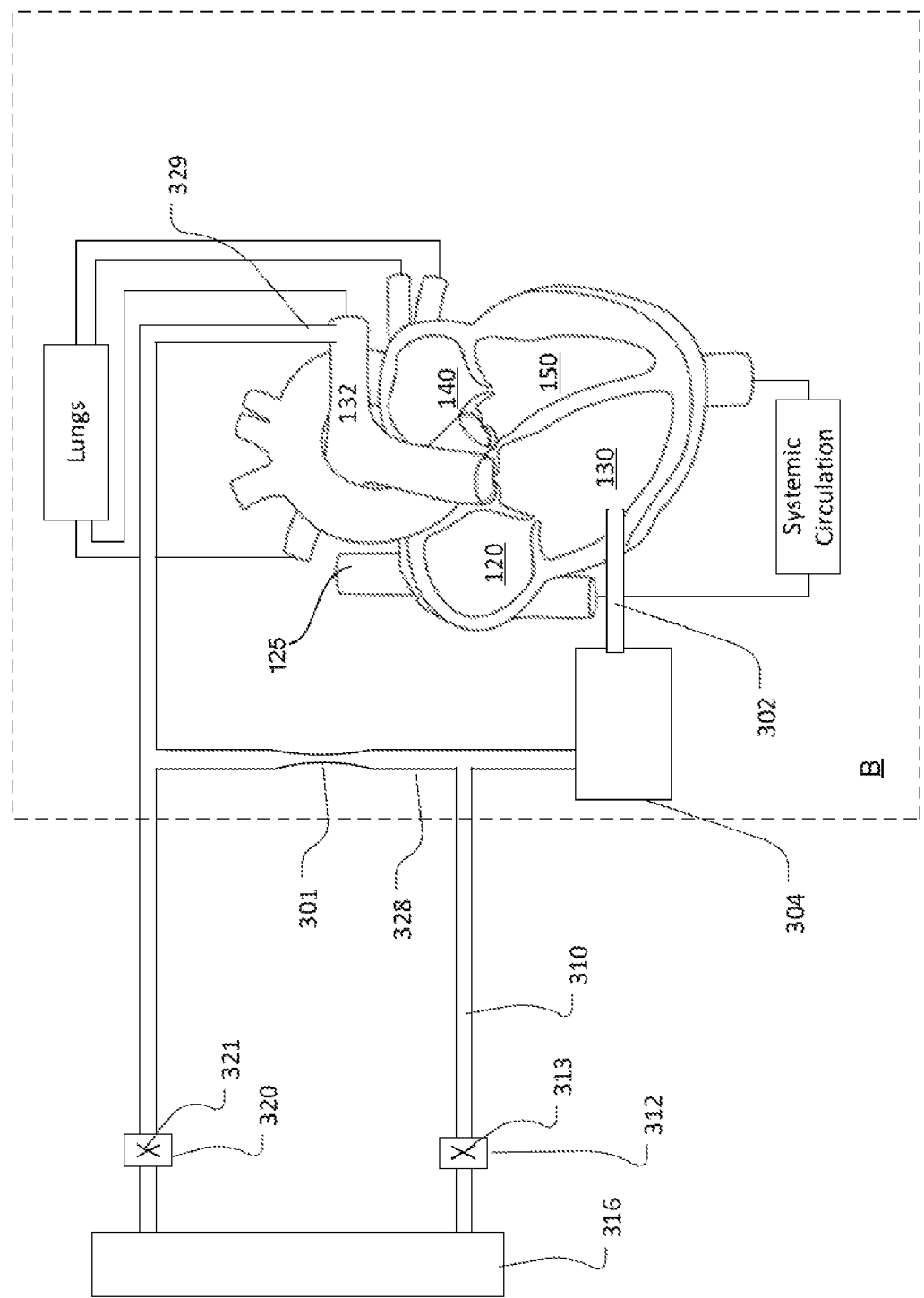
FIGS. 2 and 3 are views similar to FIG. 1 but depicting systems according to further embodiments of the invention.

A system according to a further embodiment of the invention (FIG. 2) is implanted with the inlet conduit 302 of pump 304 connected to an inlet location within the right ventricle 130 of the subject. This system uses only a single return fitting 329 connected at a single return location in the coronary artery. The system does not incorporate a valve in a branching adaptor as in the embodiment discussed above with respect to FIG. 1. In the system of FIG. 2, the bypass conduit 328 remains connected to pump 304 at all times. The bypass conduit incorporates a restriction providing resistance to flow, such as the reduced-diameter section 301. Desirably, the flow resistance along the second or bypass branch, through the bypass conduit, is greater than the flow resistance along the first branch, through conduit 310 and oxygenator 316. In the normal condition, most of the blood supplied by pump 304 passes through the first branch, and thus is oxygenated. In the bypass condition, valves 313 and 321 in disconnect fittings 312 and 320 are closed and the oxygenator 316 may be removed and replaced. While the system is in the disconnect condition, some blood continues to pass through the second branch, via bypass conduit 328. The blood flow through pump 304 and through the second branch is less than the blood flow through the pump during the normal condition, but sufficient to avoid damage to the pump or to the blood disposed within the pump.

Figure 3:
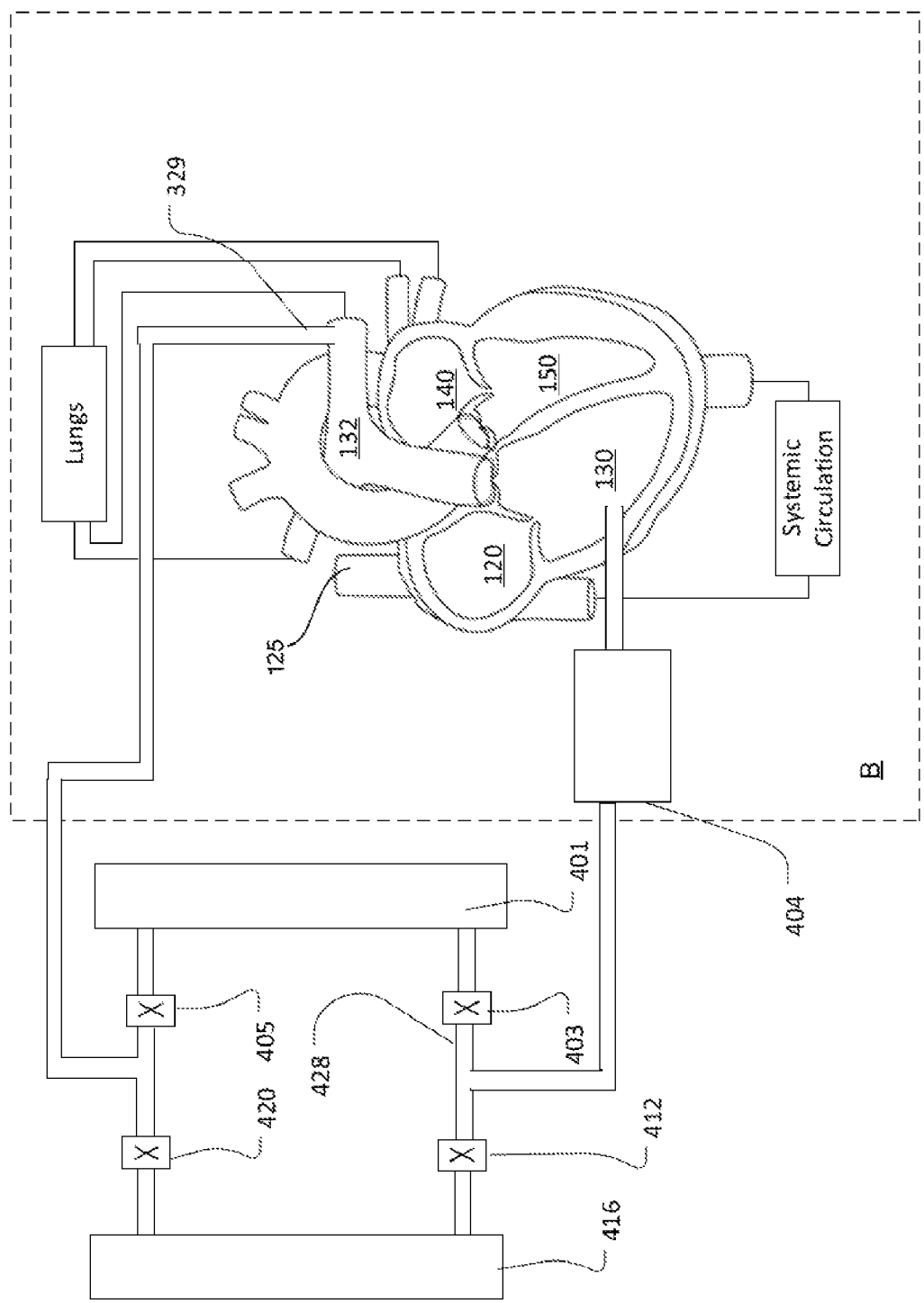

A system according to yet another embodiment of the invention (FIG. 3) is similar to the systems discussed above, except that the system of FIG. 3 has a second or bypass branch 428 which includes a second oxygenator 401 releasably connected in the second branch by valved disconnect fittings 403 and 405. As in the systems discussed above, the oxygenator 416 of the first branch is releasably connected by valved disconnect fittings 412 and 420. The system may be operated in the normal mode with valved fittings 403 and 405 closed, so that blood passes only through the first oxygenator 416. In the bypass mode, valved fittings 412 and 420 are closed and fittings 403 and 405 are opened, so that the blood passes from the pump 404 through the second branch and second oxygenator. Here again, while the system is in bypass mode, the first oxygenator can be removed and replaced. Because the system provides full oxygenation in the bypass mode, the system can be run in bypass mode for a prolonged period, which may be greater or less than the time the system is run in normal mode. When the system is in normal mode, the second oxygenator 401 can be removed and replaced. In a further variant, the system may run in normal mode with blood passing through both oxygenators, and in bypass mode with blood passing through only one of the oxygenators.

The inlet location used to supply blood to the pump may be disposed at any portion of the circulatory system. For example, the inlet location may be disposed at a portion of the circulatory system that transports unoxygenated blood, such as the vena cava or the pulmonary artery. In one example, both the inlet location and the return location may be in the pulmonary artery. A dual-lumen catheter may provide both the inlet and the return fitting. Such a catheter desirably is arranged to prevent recycling of blood from the return location back to the inlet location.

In another example, the return locations 134, 136 may be disposed at the pulmonary vein 142.

According to another embodiment of the disclosure, the oxygenator 216 may be implanted within the body B of the human subject. In this example, the entire system 200 may be implanted within the body B of the mammalian subject.

In another embodiment, the valve 208a at the adaptor (FIG. 1) may be replaced by a valve or valves connected in series with the first branch 210, in series with second branch 228, or both.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A portable lung assist system comprising:
 (a) a blood pump, wherein the blood pump has an outlet and an inlet adapted for communication with the circu- latory system of a mammalian subject at an inlet location, and wherein the blood pump can be carried by a subject;
(b) one or more return fittings adapted for communication with the circulatory system of the subject at one or more return locations remote from the inlet location;
(c) an external, portable blood oxygenator having a blood inlet releasably connectable and which is in communication with the outlet of the pump and a blood outlet releasably connectable with one of said return fittings; and
(d) a bypass conduit adapted to connect the outlet of the blood pump in communication with one of said return fittings at least when the oxygenator is disconnected, wherein the portable lung assist system supplements the action of the subject's lungs.

2. The system of claim 1 further comprising a blood oxygenator inlet disconnect fitting which is releasably connectable to the outlet of the blood pump and an oxygenator outlet disconnect fitting which is releasably connectable to one of said return fittings, the blood inlet and outlet of the oxygenator are adapted to releasably engage the disconnect fittings.

3. The system as claimed in claim 2 further comprising an adaptor having an inlet connected to the outlet of the blood pump, a first branch connected to the oxygenator inlet disconnect fitting and a second branch connected to the bypass conduit.

4. The system of claim 3, further comprising a valve in the adaptor having a a) normal condition in which blood flow entering the adaptor is directed primarily to the first branch and b) a bypass condition in which blood flow is directed primarily to the second branch.

5. The system of claim 3, wherein an internal diameter of the first branch is different than an internal diameter of the second branch.

6. The system of claim 5, wherein the internal diameter of the first branch is larger than the internal diameter of the second branch.

7. The system of claim 1, further comprising a valve connected in series with the bypass conduit, the valve having a) a normal condition in which flow through the bypass conduit is at least partially blocked and b) a bypass condition in which flow through the bypass conduit is substantially unblocked.

8. The system of claim 7, wherein when the valve is in the normal condition, flow through the bypass conduit is only partially blocked.

9. The system of claim 1, wherein the blood pump is biocompatible.

10. The system of claim 1, wherein the blood pump is selected from a group consisting of an axial-flow blood pump and centrifugal blood pump.

11. The system of claim 1, wherein at least one of the one or more return locations is selected from a group consisting of a right atrium, a right ventricle, and a pulmonary artery.

12. The system of claim 1, wherein the inlet location is a pulmonary artery.

13. The system of claim 1, wherein the bypass conduit is configured to be at least partially disposed within the subject's body.

14. The system of claim 1, wherein the blood pump is configured to pump blood out of the subject, towards the blood oxygenator.

15. The system of claim 1, wherein the blood oxygenator is wearable by the subject.

16. The system of claim 1, wherein the blood pump is a ventricular assist device.

17. The system of claim 1, wherein the blood pump is configured for long-term use by the subject.

18. A portable lung assist system comprising:
(a) a blood pump having an outlet and an inlet adapted for communication with the circulatory system of a subject at an inlet location;
(b) one or more return fittings adapted for communication with the circulatory system of the subject at one or more return locations remote from the inlet location;
(c) two external, portable blood oxygenators, wherein each portable oxygenator comprises a blood inlet releasably connectable and which is in communication with the outlet of the pump and a blood outlet releasably connectable and in communication with one of said return fittings.

19. The system of claim 18, wherein the blood pump is configured to be implanted in the subject.

20. The system of claim 18, wherein the blood pump is configured to be carried by the subject.

21. The system of claim 18, wherein the system is configured to pump blood through both oxygenators.

22. A portable lung assist system comprising:
(a) a blood pump having an outlet and an inlet adapted for communication with the circulatory system of a subject at an inlet location;
(b) one or more return fittings adapted for communication with the circulatory system of the subject at one or more return locations remote from the inlet location; and
(c) an external, portable blood oxygenator having a blood inlet releasably connectable and in communication with the outlet of the blood pump and a blood outlet releasably connectable and in communication with one of said return fittings.

23. The system of claim 22, wherein the blood pump is configured to be implanted in the subject.

24. The system of claim 22, wherein the blood pump is configured to be carried by the subject.

25. The system of claim 22, further comprising a bypass conduit adapted to connect the outlet of the blood pump in communication with one of said return fittings at least when the oxygenator is disconnected.

26. The system of claim 22, further comprising a second external, portable blood oxygenator having a blood inlet releasably connectable to and in communication with the outlet of the pump and a blood outlet releasably connectable in communication with one of said return fittings.

27. A method of providing respiratory assistance to a subject comprising:
(a) directing blood from an inlet location in the circulatory system of the subject through a blood pump, out of the subject, through a first and second external, portable oxygenator and back to the circulatory system;
(b) disconnecting the first external, portable oxygenator;
(c) directing blood through the blood pump, and through the second external, portable oxygenator, back to the circulatory system; and
(d) reconnecting either (i) the first external, portable oxygenator from (a), or (ii) a different first external, portable oxygenator.

28. The method of claim 27, wherein (b), (c) and (d) are performed so that blood continuously flows through the pump.

29. The method of claim 27, wherein in (c), the blood is directed back to the pulmonary artery of the subject.

30. The method of claim 29, wherein in (a), the blood is directed back to the pulmonary artery of the subject.

31. The method of claim 27, wherein (a) further comprises simultaneously directing blood through a bypass conduit and back to the circulatory system.

32. The method of claim 31, wherein during (a), blood passes through the oxygenator at a first rate and blood passes through a bypass conduit at a second rate less than the first rate.

* * * * *